United States Patent
Wassermeier et al.

(10) Patent No.: US 8,726,746 B2
(45) Date of Patent: May 20, 2014

(54) METHOD FOR CHECKING THE STATE OF A PIPETTE, PIPETTING METHOD, PIPETTING DEVICE, AND SUCTION TUBE FOR A PIPETTING DEVICE

(75) Inventors: Matthias Wassermeier, Munich (DE); Zeno Von Guttenberg, Munich (DE); Frido Roehrs, Hamburg (DE)

(73) Assignee: Beckman Coulter, Inc., Brea, CA (US)

( * ) Notice: Subject to any disclaimer, the term of this patent is extended or adjusted under 35 U.S.C. 154(b) by 284 days.

(21) Appl. No.: 12/867,863

(22) PCT Filed: Jan. 22, 2009

(86) PCT No.: PCT/EP2009/000380
§ 371 (c)(1),
(2), (4) Date: Aug. 16, 2010

(87) PCT Pub. No.: WO2009/103392
PCT Pub. Date: Aug. 27, 2009

(65) Prior Publication Data
US 2011/0000276 A1    Jan. 6, 2011

(30) Foreign Application Priority Data

Feb. 18, 2008  (DE) .......................... 10 2008 009 626

(51) Int. Cl.
*B01L 3/02* (2006.01)
*G01F 25/00* (2006.01)

(52) U.S. Cl.
USPC ........................................ 73/864.01; 73/1.74

(58) Field of Classification Search
CPC ....... G01N 9/002; G01N 11/16; G01N 29/11; G01N 29/12; G01N 29/036; G01H 9/008; G01H 11/08
USPC ................... 73/1.73, 864.01, 864.02, 864.11, 73/864.13, 864.24, 64.53, 290 V, 579
See application file for complete search history.

(56) References Cited

U.S. PATENT DOCUMENTS 2,768,524 A    10/1956    Beard
4,283,950 A     8/1981    Tervamäki
(Continued)

FOREIGN PATENT DOCUMENTS

DE    4 313 216 C2    12/1995
EP    1 596 169 A1    11/2005
(Continued)

OTHER PUBLICATIONS

English Machine Translation, Isamu et al, JP 2000-157543 A, Ultrasonic Wave Probe, translated Aug. 2013.*

(Continued)

*Primary Examiner* — Hezron E Williams
*Assistant Examiner* — David Z Huang
(74) *Attorney, Agent, or Firm* — Kilpatrick Townsend & Stockton LLP

(57) ABSTRACT

The invention relates to a method for checking the state of a pipette, which pipette includes a suction tube and a pipette tip. According to the invention, ultrasound is coupled into the wall of the suction tube and the damping of the ultrasonic signal is measured as a function of the frequency. The measured frequency-dependent damping is compared with at least one reference measurement or a calibration curve based on the reference measurements, in order to determine whether the pipette is in a functional condition and/or whether the pipette contains or has made contact with fluid. Furthermore, the invention relates to a pipetting method which uses the inventive method for checking the state, a suction tube arrangement for a pipetting device for pipetting fluid, and a pipetting device with which the inventive methods can be carried out.

44 Claims, 5 Drawing Sheets

(56) References Cited

U.S. PATENT DOCUMENTS

| | | | |
|---|---|---|---|
| 4,864,856 A | 9/1989 | Ichikawa et al. | |
| 5,983,723 A | 11/1999 | Buckin et al. | |
| 6,232,129 B1 | 5/2001 | Wiktor | |
| 7,416,706 B2* | 8/2008 | Brunner et al. | 422/106 |
| 2003/0140695 A1* | 7/2003 | Fehrenbach | 73/290 V |
| 2005/0210965 A1* | 9/2005 | Sinha | 73/61.79 |
| 2006/0093525 A1 | 5/2006 | Brunner et al. | |
| 2007/0199379 A1* | 8/2007 | Wolf et al. | 73/590 |
| 2007/0272209 A1* | 11/2007 | Matsiev et al. | 123/350 |

FOREIGN PATENT DOCUMENTS

| | | |
|---|---|---|
| JP | 2000-157543 A | 6/2000 |
| WO | WO 97/02893 A1 | 1/1997 |

OTHER PUBLICATIONS

International Search Report from PCT/EP2009/000380, dated Jul. 6, 2009 (4 pages).

International Preliminary Report on Patentability for Application No. PCT/EP2009/000380, dated Sep. 7, 2010, 8 pages.

English translation of Russian office action dated Dec. 25, 2012 for Russian patent application No. 2010138578/28(055107), 4 pages.

English Translation of Japanese Unexamined Patent Application Publication 05-281241, Translation Jun. 21, 2013, 4 pages.

English Translation of Office Action dated Apr. 19, 2013, mailed on Apr. 23, 2013 for Japanese Application No. 2010-546229, 4 pages.

\* cited by examiner

METHOD FOR CHECKING THE STATE OF A PIPETTE, PIPETTING METHOD, PIPETTING DEVICE, AND SUCTION TUBE FOR A PIPETTING DEVICE

CROSS-REFERENCE TO RELATED APPLICATIONS

The present application is a U.S. National Phase of PCT/EP2009/000380, filed Jan. 22, 2009, which claims the benefit of German Application No. 10 2008 009 626.1, filed on Feb. 18, 2008, the disclosures of which are hereby incorporated herein by reference in their entirety.

The invention relates to a method for checking the state of a pipette, which comprises a suction tube and a pipette tip; a pipetting method, which uses such a method; a pipetting device; and a suction tube arrangement for a pipetting device, with which these methods can be carried out.

For example, it is often necessary during analysis to meter very small quantities of fluid with a high degree of precision. To this end pipettes are usually used. It is precisely in the case of automated pipetting methods that it is important to know exactly the state of the pipette—that is, the correct functionality or the fill volume. In addition, it can be useful to know the point in time, at which on approaching a fluid the pipette makes contact with the surface of the fluid.

According to a method described in U.S. Pat. No. 5,428,997, the pin-shaped end of an ultrasonic transducer is immersed in the fluid. The ultrasonic resonant frequency is observed in order to obtain a measure for the point in time of the immersion. US 2003/0200801 A1 describes a method, wherein the tip of a pipette has two concentric electrodes, which are short circuited on contact with the fluid and, thus, can output a signal about reaching the fluid surface. Other methods use conductive pipette tips, the capacitance of which changes when immersed in the fluid.

In order to minimize the risk of contamination for the fluid owing to the immersion, interchangeable pipette tips are used for example. Since the disposable tips have to be especially designed, for example, as conductive tips or have to be fitted with separate electrodes, high costs may be incurred.

A method described in U.S. Pat. No. 5,705,750 measures the distance from a fluid surface by evaluating the runtime of an ultrasonic pulse, sent in the direction of the fluid surface, to which end a suitable measuring system is necessary.

U.S. Pat. No. 5,465,629 describes an immersion sensor, where the air column in the interior of the pipette is driven into oscillation. Depending on whether the intake orifice of the pipette is open or closed, when the pipette is located, for example, in the fluid, the oscillation characteristic of the air column in the suction tube of the pipette changes. In order to excite the oscillation in the air column, a sound source is required. If, on the other hand, the immersion time is determined by a detectable increase in pressure in the interior of the pipette, then a defined air flow through the intake orifice of the pipette has to be set with a very high degree of accuracy.

The object of the present invention is to provide a method for checking the state of a pipette, a pipette method, a suction tube arrangement for a pipetting device and a pipetting device—all of which make possible a precise pipetting operation in a simple and cost effective way.

This engineering object is achieved with a method that is intended for checking the state of a pipette and that exhibits the features disclosed in claim 1; a pipetting method exhibiting the features disclosed in any one of the claim 17, 20, 21, 22 or 23; a suction tube arrangement that is intended for a pipetting device and that exhibits the features disclosed in claim 24; or a pipetting device exhibiting the features disclosed in claim 35.

Advantageous embodiments are the subject matter of the dependent claims.

The method according to the invention serves to check the state of a pipette, which comprises a suction tube and a pipette tip. Ultrasound is coupled into the wall of the suction tube and the damping of the ultrasonic signal is measured as a function of the frequency. The measured frequency-dependent damping is compared with at least one reference measurement of the frequency-dependent damping or a calibration curve based on the reference measurements. This comparison is used to determine whether the pipette is in a functional condition and/or whether the pipette contains or has made contact with fluid.

A deviation from the expected course can be used, for example, to generate a warning signal.

Therefore, the method according to the invention uses the damping of the ultrasonic signal, which is generated when the ultrasound is coupled into the wall of the pipette, for the purpose of detection. The oscillation, which is excited by the ultrasound in the system, which comprises the wall, the pipette tip and the ultrasonic transducer, reacts with high sensitivity to changes in the state of the pipette. If, for example, the pipette is damaged or a part is missing—for example, the tip of the pipette—then this fact is reflected in the damping of the ultrasonic signal. In addition, the oscillations that are excited in the system react with high sensitivity to an additional mass accumulation, which occurs, for example, when the pipette is dipped into a fluid or when fluid is aspirated into the pipette.

In order to measure the frequency-dependent damping, an ultrasonic signal can be outputted in a frequency range having a specific bandwidth, for example, and the measured signal can be evaluated by means of a frequency analyzing measuring device—for example, a network analyzer. In another variant of the method the coupled frequency is changed over time.

It is possible to compare, for example, certain selected characteristics, individual values or the progression of the measured frequency-dependent damping signal and the reference measurement. A reference measurement can also comprise the determination of one or more threshold values, of which the overshooting or undershooting by the respective measurement values can be evaluated for the purpose of detection.

Another option is also to use a calibration curve, which is a combination of reference measurements under a variety of conditions, for the comparison.

The at least one reference measurement for the comparison of the measured frequency-dependent damping can be performed with a structurally identical pipette. However, it is especially advantageous if the pipette is used with the suction tube and the pipette tip, which is also used during the actual measurement, in order to avoid any errors owing to the different designs of the pipettes.

The frequency-dependent damping can be measured, for example, at defined times. Advantageous is a continuous measurement of the damping signal in order to enable monitoring without interruption.

It is advantageous to select for the measurement a frequency range, in which there is at least one eigen mode of the system that is used. Then it is possible to compare in a simple way, for example, the value of the resonant frequency of the measured damping signal with the value of the resonant frequency of a reference measurement or with a calibration curve, which is based on the resonant frequencies under different conditions. In another embodiment the resonance amplitude of the eigen mode is compared. It is also possible to use characteristics of an eigen mode for the comparison, such as the width at half maximum or the area of the eigen mode.

In this respect it is especially advantageous if the arrangement for carrying out the method is selected in such a manner that the ultrasound is coupled into the wall of the suction tube in such a way that predominantly the transversal modes are excited. To this end it is advantageous if, for example, the piezo actuator is mounted on the suction tube in such a way that preferably shearing motions are carried out on the suction tube. Transversal modes exhibit, for example, a very high sensitivity to a mass accumulation that occurs when the pipette tip dips into the fluid.

A simple embodiment of the method according to the invention provides that a piezo actuator is used in order to couple the ultrasound into the wall of the suction tube. A piezo actuator is cost effective and can be mounted, for example, on the outside wall of the suction tube. It can comprise, for example, a ceramic made of lead, zirconate and titanate.

In order to enhance the sensitivity of the actuator, for example, to the time of the immersion, the immersion depth or the fill level of the pipette, an additional mass can interact with the piezo actuator. Such an additional mass can increase, for example, the amount of change in the frequency or damping on immersion of the pipette and/or on aspiration of the fluid into the pipette or on ejection of the fluid from the pipette.

A simple embodiment of the method provides that an additional mass is used that is mounted or simply adhesively cemented on the side of the piezo actuator that faces away from the suction tube. Especially advantageous is an additional mass that corresponds to 0.1 to 10 times, preferably 0.5 to 2 times, the weight of the suction tube.

The piezo actuator can be used advantageously not only as an ultrasonic transmitter, but also as a receiver for the damped ultrasonic signal.

The frequency range that is used for the ultrasonic signal is determined by the special properties of the geometry of the pipette that is used—therefore, in particular, the dimensions and the materials of the suction tube, the pipette tip that is used and additional mass that may or may not be present. In this case it is advantageous to select a frequency range, in which an eigen mode can be excited. A high sensitivity can be reached, for example, if the ultrasonic frequencies are selected from a range, which corresponds to 1 to 10 times the quotient composed of the speed of sound in the pipette material and a characteristic geometric expansion of the pipette, in particular its length.

In order to avoid the risk of contamination, it is advantageous to use disposable pipette tips. To this end it is possible to use two-part pipettes, where a first part comprises the suction tube and the second part, which is configured advantageously so as to be detachable, comprises the pipette tip.

The inventive method for checking the state can determine, in particular, in the case of two-part pipettes, whether the pipette is complete. It is precisely in automated methods using disposable pipette tips that the method can be used advantageously, because the presence of the pipette tip can be carried out without a visible inspection by the operating personnel. The absence of the pipette tip is reflected in the frequency-dependent ultrasonic damping of the suction tube and, thus, is easily detectable. This feature is especially advantageous in the case of automated pipette methods, where a plurality of pipettes are operated in parallel by a robot.

The inventive method for checking the state of a pipette can be used advantageously with pipetting methods. For example, the method according to the invention can check the state of a pipette, for example, as to whether the pipette tip is making contact with a fluid to be pipetted. To this end, the measured frequency-dependent damping can be compared with a reference measurement of the frequency-dependent damping, which was carried out on a pipette that is not making contact with a fluid. For example, a displacement or a flattening off of the resonant frequency signal can be detected with a very high degree of precision, so that the immersion time can be exactly determined.

After detecting in this way the immersion of the pipette tip into the fluid, the fluid is aspirated into the pipette. Then the fluid can be conveyed to a different site with the pipette and can be ejected again from the pipette.

This procedure for carrying out the method is especially easy if the pipette with the suction tube and the pipette tip is lowered in the direction of the fluid from a point above the surface of the fluid to be pipetted. During this lowering operation the frequency-dependent damping can be measured, in order to obtain in this way a reference signal prior to immersion. If one continues to lower the pipette, the result is that the pipette tip makes contact with the surface of the fluid, which in turn changes the frequency-dependent damping signal. Therefore, in this advantageous embodiment the frequency-dependent damping is measured while the pipette is being lowered in the direction of the fluid, in order to determine the point in time, at which the pipette tip hits the fluid surface, from a change in the frequency-dependent damping signal.

In order to be able to characterize the pipetting procedure, one embodiment of the invention infers the state of the pipette with respect to the immersion depth in a fluid from the frequency-dependent damping signal. The further the pipette tip dips into the fluid, the more intensive is the change in the frequency-dependent damping signal in relation to a reference measurement, during which the pipette is located outside the fluid.

In an additional pipetting method according to the invention, the frequency-dependent damping signal is monitored during the aspiration of the fluid into the pipette, in order to obtain in this way information about the amount of fluid that has already been aspirated and that also has an impact on the frequency-dependent damping. Then the aspirated fluid can be conveyed to a different location with the pipette and can be dispensed again.

Finally another pipetting method according to the invention determines very precisely from a frequency-dependent damping signal, which is monitored during the dispensing of the fluid from the pipette, when the pipette has reached the state of total emptiness at the end of the pipetting operation. In order to carry out this method the frequency-dependent reference signal is monitored during the ejection process.

Another pipetting method according to the invention uses the inventive method for checking the state of the pipette, in order to determine the type of fluid that is in the pipette during the pipetting operation. Different fluids with, for example, different densities have different effects on the ultrasonic damping behavior of the suction tube, in which the fluids are located. In this respect the damping signal of the suction tube can also be used to determine the type of fluid through a comparison with the respective reference measurements. Other physical or chemical properties of the fluid, which may have an impact on the damping of the suction tube that contains the fluid, can be used for the characterization.

Especially if the inventive methods for determining the immersion time are used for monitoring the fill level or the ejection process, it is possible to combine several reference measurements in an advantageous manner in order to construct a calibration curve.

The invention also comprises, in particular, the combination of two or more of the claimed inventive pipetting methods and/or the methods for checking the state during a pipetting operation.

The inventive suction tube arrangement for a pipetting device for pipetting fluid has an ultrasonic transducer, which is mounted on a suction tube and serves to couple an ultrasound into the wall of the suction tube. An actuating device is used to actuate the ultrasonic transducer in order to output an ultrasonic signal in a predefined frequency range and there is a receiving device for receiving the damped ultrasonic signal.

Finally the suction tube arrangement according to the invention has a suction device, by means of which a negative pressure can be generated in the suction tube, in order to aspirate fluid into or through the suction tube. In this case it may involve, for example, a pipette suction piston, which is guided in the suction tube.

Such a suction tube arrangement according to the invention can be used, in particular, for the inventive pipetting methods and the inventive method for checking the state. In particular, it is possible to use disposable pipetting tips, which are fitted on the suction tube, in order to form a pipette together with the suction tube. The coupling of the ultrasonic signal into the wall of the suction tube and the measurement of the damped ultrasonic signal can be used in the way described to carry out the methods according to the invention.

Advantageous embodiments of the suction tube arrangement according to the invention are apparent in an analogous manner from the described embodiments of the inventive methods and their advantages.

In particular, in order to carry out a frequency-dependent measurement in conjunction with the suction tube arrangement according to the invention, the actuating device and the receiving device can be configured so as to actuate or to receive a wideband ultrasonic signal or an ultrasonic signal that can vary over time.

One advantageous embodiment of the suction tube arrangement according to the invention provides an evaluating device, which is configured so as to evaluate as a function of the frequency the damped ultrasonic signal, preferably with respect to its resonant frequency and/or its resonant amplitude. With an evaluating device of this type the pipetting operation and the monitoring of the pipetting operation can be automated in an easy way.

The evaluating device can also comprise a memory unit, in which the data from the reference measurements or the calibration curves, constructed from said data, are filed for comparison purposes.

If the suction tube arrangement according to the invention provides the ultrasonic transducer on the outside of the wall of the suction tube, then a contamination of the ultrasonic transducer by the fluid is avoided.

The use of an additional mass, which interacts with the ultrasonic transducer—in particular, is adhesively cemented to the ultrasonic transducer—can serve to enhance the sensitivity of the ultrasonic transducer. An advantageous order of magnitude for the additional mass is in the range of 0.1 to 10 times, preferably 0.5 to 2 times, the weight of the suction tube.

Especially cost effective and simple is the use of a piezo actuator as the ultrasonic transducer.

The suction tube arrangement according to the invention can be an integral component of a whole pipette. However, especially advantageous is the use of a suction tube arrangement according to the invention in a pipetting device comprising an at least two-part pipette, where a first part comprises the suction tube arrangement according to the invention and a second part comprises a pipette tip. In order to be able to readily exchange the pipette tip, which can be configured, for example, as a disposable part, it is especially advantageous if the two parts of the pipetting device are designed so as to be detachable from each other, in order to make the replacement process of the pipette tip easy.

The invention is explained below by means of various examples of the ways to carry out the invention as well as embodiments with reference to the schematic figures. In them FIG. 1 shows the bottom area of a pipetting device that is designed in accordance with the invention.

Figure 1:
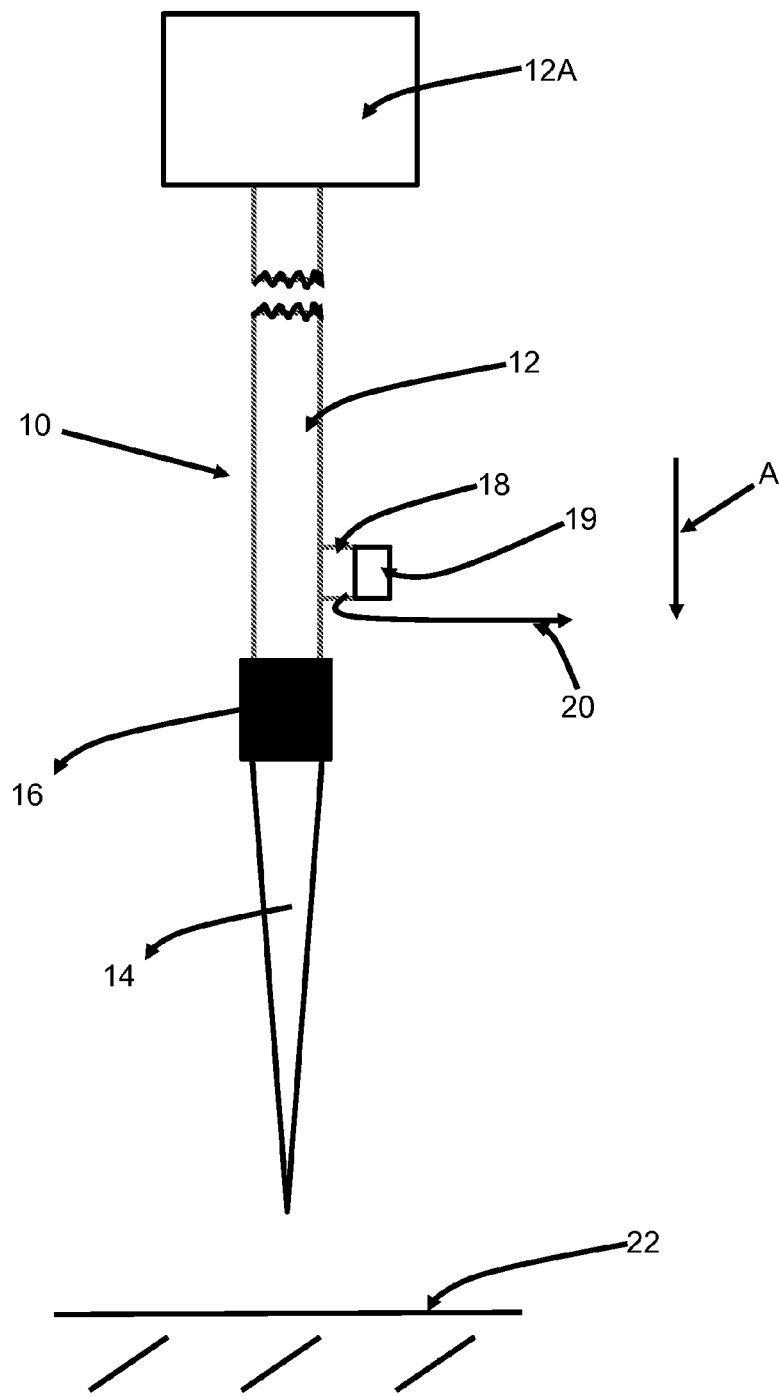

FIG. 1 shows the bottom end of a pipette 10 with a pipette tip 14. The pipette tip exhibits a collar 16, with which it is fitted on a suction tube 12. The pipette tip 14 is made, for example, of polypropylene.

The suction tube 12, which is only partially shown, can be used in a fully automated robotic system for pipetting. The suction tube 12 has in a manner known from the prior art a suction piston, which can be driven by way of a motorized spindle, in order to aspirate fluid into the pipette and/or eject fluid from the pipette.

An additional embodiment provides the piston in an external device, which is connected to the suction tube via a hose. As an alternative, a suction device—for example, a suitable pump—can be connected to the suction tube.

Reference numeral 18 denotes a piezoelectric actuator, which is used as the ultrasonic transmitter and ultrasonic receiver. It is advantageous to use an element made of a piezoelectric material—for example, a ceramic composed of lead, zirconate and titanate. The piezoelectric actuator 18 is connected to an actuating and evaluating unit (not shown), which comprises, for example, a suitably programmed microprocessor, by way of a supply line 20, which has, for example, two thin cables.

The piezo actuator 18 is attached to the suction tube 12 by means, for example, of an epoxide adhesive. It is configured in such a way that it exerts preferably a shearing motion on the suction tube 12, so that predominantly transversal modes are excited.

The side of the piezo actuator 18 that faces away from the suction tube 12 can exhibit an additional mass 19, in order to enhance the sensitivity of the piezo actuator. The additional mass can be equal, for example, to 0.1 to 10 times the weight of the suction tube.

The piezoelectric actuator is selected in such a way that it can excite the oscillations, especially in the frequency range of the eigen modes of the system, composed of the suction tube 12 that is used with the affixed pipette tip 14, the actuator 18 and optionally the additional mass 19. Such eigen modes are typically in a range of 10 to 80 kHz, which can be readily excited with piezoelectric elements made of lead, zirconate and titanate.

The measurement system, which comprises the actuating and evaluating unit, is configured in such a manner that a defined power can be sent to the piezo actuator 18 at a high frequency interval and the damped ultrasonic signal, which arrives again at the piezo actuator 18, can be measured. In this case the sensitivity is, for example, in a range of 10 µV. In order to be able to measure the damping as a function of the frequency, the evaluating device comprises, for example, a network analyzer. The evaluating device is configured so as to compare a measurement or the characteristic measured values with the reference measurements, which are filed in a memory unit, or with the calibration curves that are constructed from said measurements.

FIG. 1 shows the pipette 10 in a state, in which it is located just above the fluid surface 22 of a fluid that is to be pipetted. To this end, the pipette can be lowered in the direction A onto the fluid surface 22 by means, for example, of a pipetting robot.

The suction tube 12 is suspended in the pipetting robot in such a way, for example, that the oscillation is damped as much as possible, so that the oscillations generated in the mechanical design of the robot are not transferred to the pipette and so that the measurement of the damped ultrasonic oscillations with the piezo actuator 18 would be falsified. In this example the suction tube 12 is not rigidly attached in the pipetting robot, so that the eigen modes, which are excited with the piezo actuator 18 and their damping is used for the measurement, are not impeded by the rigid attachment. However, a rigid attachment is not ruled out, if the oscillations that might be produced by the robot are sufficiently small or are considered in the evaluation of the measurement.

A pipette, as shown in FIG. 1, is used as follows.

Figure 2:
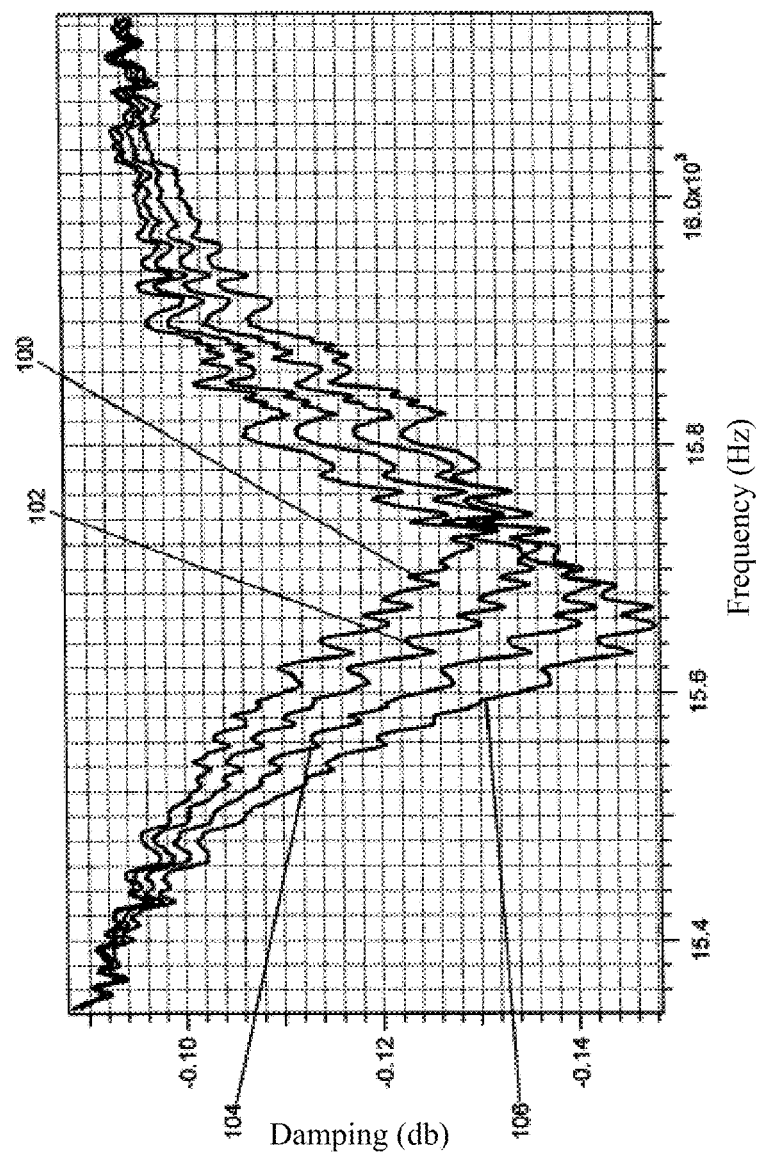
FIG. 2 shows the frequency-dependent damping signal at various depths of immersion.

The actuating and evaluating unit feeds a high frequency signal, which is, for example, in a frequency range of 10 to 80 kHz, through the supply lines 20 into the piezo actuator 18, thus exciting the natural oscillations in the suction tube 12. In FIG. 2 the curve 100 shows, for example, the damping in decibels. This damping is measured in a pipette that is located above the fluid level 22 and, hence, is immersed 0 mm in the fluid. The figure shows the damping of the coupled ultrasonic oscillation generated by the excitation of the eigen mode in the system comprising the suction tube 12 with the pipette tip 14, the actuator 18 and an additional mass 19 that may or may not be present. Shown are the measurements with a 1 ml pipette.

The excited oscillations in the suction tube 12 trigger a deformation of the piezoelectric actuator, as a result of which electric voltages are induced in this actuator. With a suitable measuring device the electric response of the system is compared with the high frequency excitation signal. In this case when an eigen mode is excited, the difference is the greatest. The eigen mode is determined predominantly by the properties of the suction tube 12, the pipette tip 14 and the additional mass 19 that may or may not be present or by the mass accumulation of the elements by the fluid to be pipetted.

The pipette 10 is now moved in the direction A towards the fluid surface 22 with, for example, the pipetting robot. The moment at which the tip makes contact with the fluid, the damping changes. The resonant frequency shifts and the resonance amplitude becomes smaller. In FIG. 2 this is shown with the example of varying immersion depths. The reference numeral 102 shows the signal for a pipette, which is immersed 1 mm into the fluid; the reference numeral 104 shows the signal for a pipette, which is immersed 2 mm into the fluid; and the reference numeral 106 shows the signal for a pipette, which is immersed 3 mm into the fluid.

Figure 3:
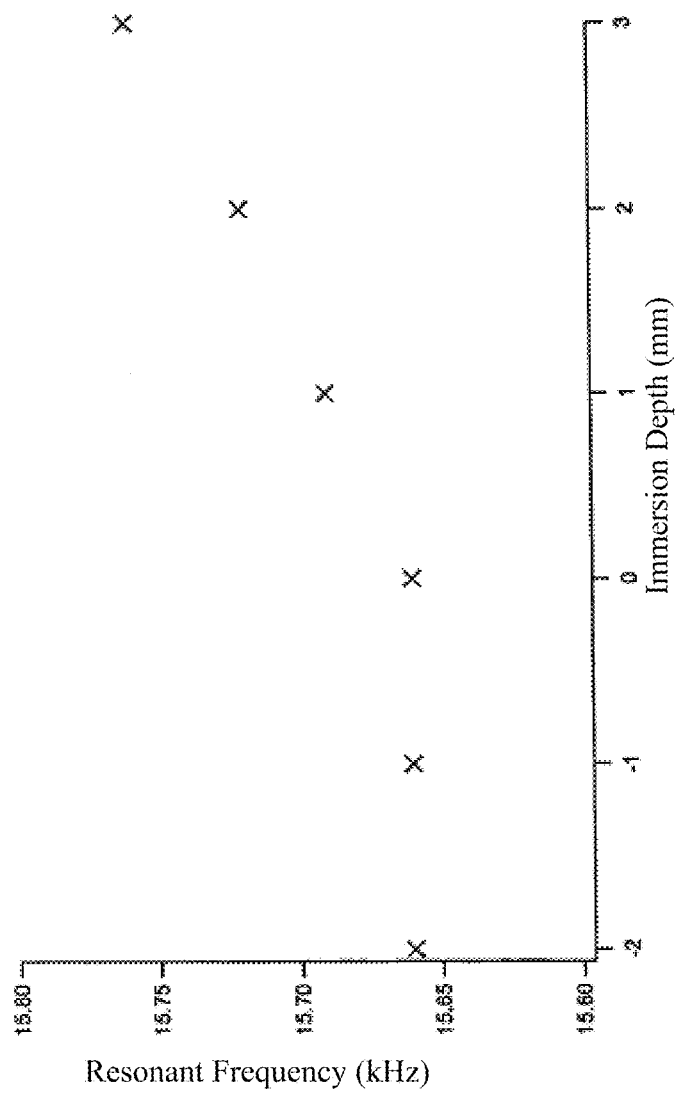
FIG. 3 shows a graph of the resonant frequency as a function of the immersion depth of the pipette.

The result is a relationship between the damping and the resonant frequency, as plotted in the form of a graph in FIG. 3. The negative values for the immersion depth stand for the measurements, where the pipette is at a respective distance above the fluid surface, and are, thus, the same among each other. A graph, like the one shown in FIG. 3, can be used, for example, as the calibration curve, if desired, after the plotted reference points were curve fitted.

If the resonant frequency of the damping signal shifts in the direction of larger frequencies, this shows that the pipette is immersed in the fluid. The immersion depth itself can be determined, for example, by means of a graph as shown in FIG. 3.

As soon as the pipette 10 touches the fluid 22 with the tip 14 or is immersed in it, a pipetting robot is employed to aspirate the fluid into the pipette in a manner that is well known from the prior art by means of the suction piston. In the interim the frequency-dependent damping of an ultrasonic signal, which is coupled into the wall of the suction tube 12 by means of the piezo actuator 18, can be measured. The respective measurement curves are shown for a 1 ml pipette in FIG. 4 for illustrative purposes. The reference numeral 200 denotes a measurement curve of the frequency-dependent damping signal when the pipette is empty. The reference numeral 202 denotes the measurement of a pipette that is filled with 25 µl of fluid. The reference numeral 204 denotes a measurement curve for a pipette that is filled with 50 µl of fluid, whereas 206 shows a measurement curve for a pipette that is filled with 75 µl of fluid. Finally the reference numeral 208 denotes the measurement of the damping at a pipette that is filled with 100 µl of fluid, whereas 210 denotes a curve that was constructed from the measurement of a pipette that was filled with 150 µl of fluid. The result is a relationship for the frequency-dependent damping signal as a function of the fill volume that is shown in FIG. 5.

This graph shows the exact volume in the pipette in relation to the measured resonant frequency. In addition, a graph, like the one shown in FIG. 5, can be used, for example, as the calibration curve, if desired, after the plotted reference points have been curve fitted.

During the ejection process of the pipette, it can also be determined with a high degree of accuracy whether and/or when the fluid has issued in its entirety from the pipette. To this end, the frequency-dependent damping can also be monitored and by comparing with a reference measurement or a calibration curve, according, for example, to FIG. 5, it can be determined when the signal matches the signal of the empty pipette.

Figure 4:
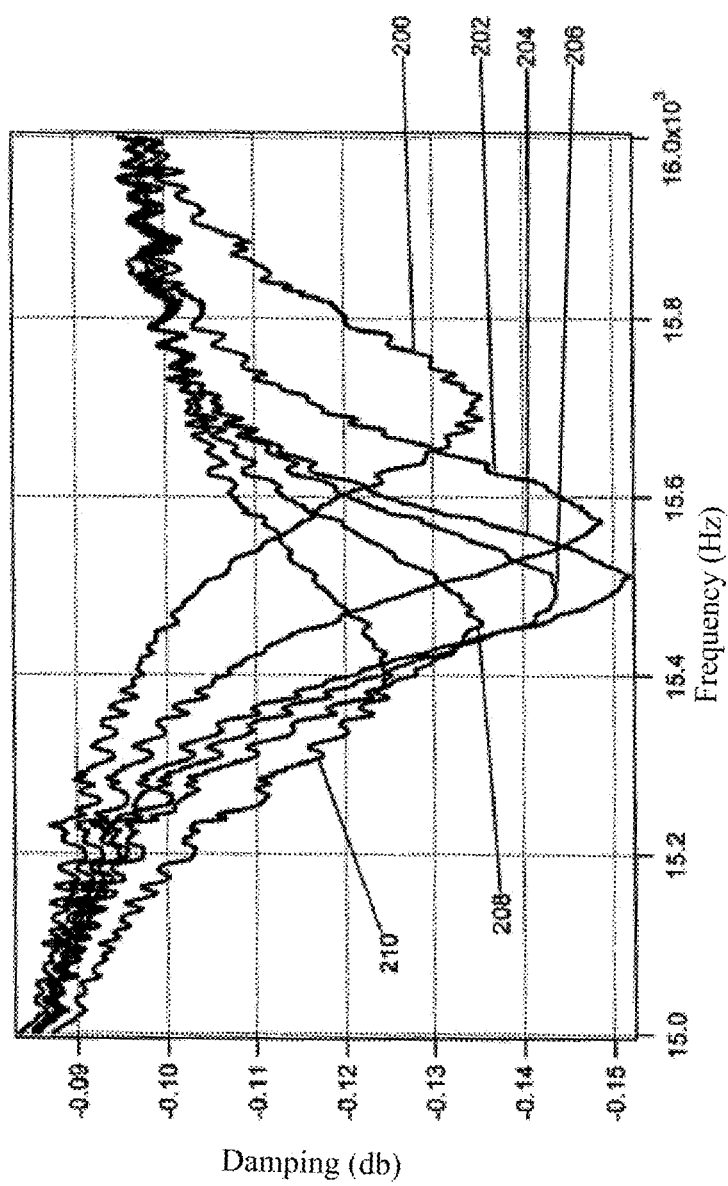
FIG. 4 shows the frequency-dependent damping for various fill volumes of the pipette.
Figure 5:
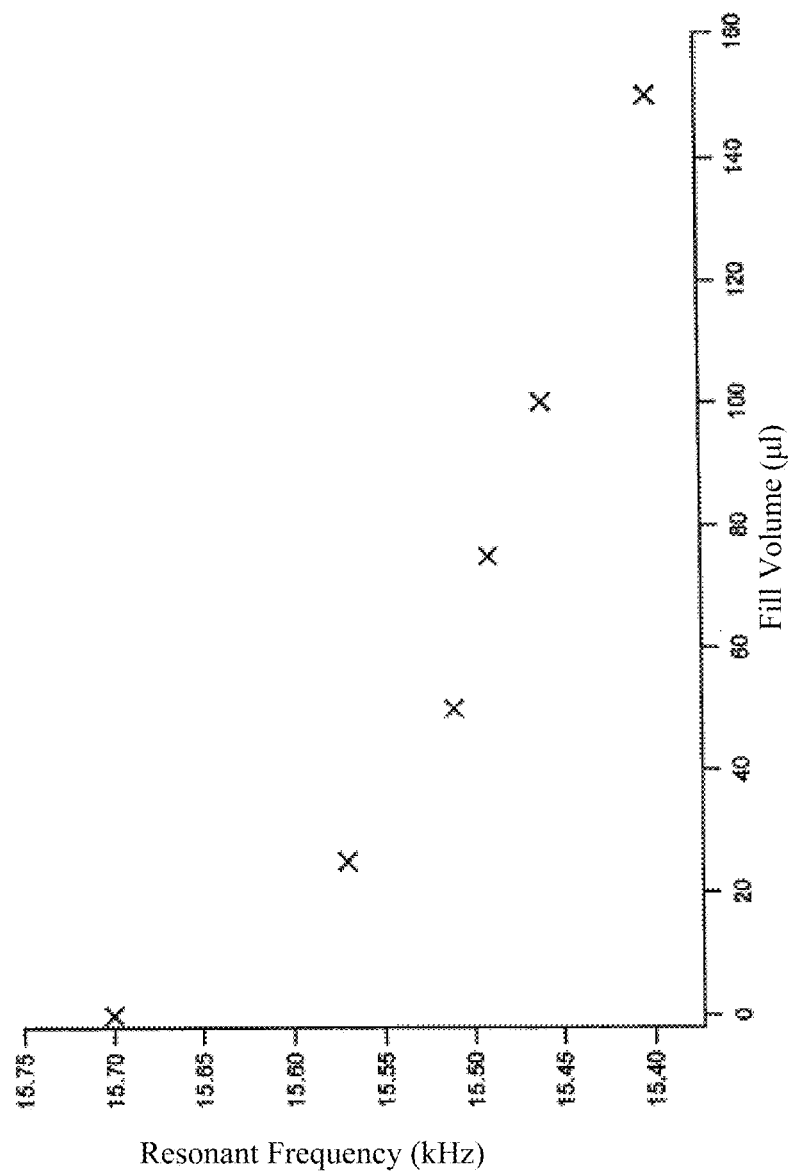
FIG. 5 shows a graph of the resonant frequency as a function of the fill volume.

At variance with the graphs shown herein, it is also possible to evaluate, for example, the resonance amplitude, which also depends on the immersion depth or the fill volume, as is evident from FIGS. 2 and 4. Other methods serve to evaluate the area of the resonance curve or the width at half maximum.

The sensitivity of the piezo actuator 18 to the point in time of the immersion, the immersion depth and the fill volume in the pipette can be enhanced by an additional mass ranging from, for example, 0.1 to 10 times the weight of the suction tube. This additional weight is adhesively cemented on the side of the piezo actuator 18 that faces away from the pipette. Such an additional mass increases the amount of change in the frequency or damping when the pipette is immersed in the fluid or the fluid is aspirated into the pipette or the fluid is ejected from the pipette.

The inventive method for checking the state can verify before and during the pipetting operation whether the pipette is in a proper state. For example, an error or leakiness in the pipette tip or in the suction tube is expressed in the measured frequency-dependent damping signal. Even if no pipette tip 14 is affixed on the suction tube 12, it has an effect on the frequency-dependent damping signal, which deviates from a respective reference measurement.

After a pipetting operation, the simple and cost effective pipetting tip, which is made, for example, of polypropylene, can be replaced, in order to avoid contamination of the fluid of future measurements.

In the inventive method and the inventive devices, ultrasound is coupled into the wall of the suction tube 12. The coupling into the suction tube is readily possible and simpler than, for example, the coupling into the pipette volume. This coupling can be achieved with a piezo actuator in an easily accessible frequency range. The pipette tip does not have to exhibit any special design or special materials, so that it can be configured as a disposable element.

Especially advantageous is its application in conjunction with automated pipetting methods. In this case a pipetting robot is used to fill in parallel, as required, a very large number of multiple pipettes and to dispense the aspirated fluid. In this respect it is especially important that the individual pipettes be checked and monitored with a high degree of accuracy, because a visual inspection by an operating person is not performed as a rule. The inventive methods and the inventive devices are especially suitable for such tasks, because they allow the functionality and state to be checked precisely. In addition, the fill level in the pipette and/or the type of fluid contained in the pipette can be easily determined. One important application is, for example, the pooling of blood samples.

List of Reference Numerals and Symbols

10 pipette
12 suction tube
12A suction device
14 pipette tip
16 collar
18 piezo actuator
19 additional mass
20 supply lines
22 fluid surface
100, 102, 104, frequency-dependent damping signals
106, 200, 202,
204, 206, 208,
210
A lowering direction

The invention claimed is:

1. A method for checking the state of a pipette, the pipette comprising a suction tube and a pipette tip, the method comprising:
   coupling an ultrasonic signal into the wall of the suction tube, wherein said ultrasonic signal is generated by a piezo actuator disposed between said wall of said suction tube and an additional mass, said piezo actuator mounted on said wall of said suction tube, said piezo actuator in contact with said additional mass on a side facing away from said suction tube;
   measuring the frequency-dependent damping of the ultrasonic signal in the wall of the suction tube in a predefined frequency range comprising a plurality of frequencies as a function of the frequency;
   comparing the measured frequency-dependent damping in the predefined frequency range with at least one reference measurement of the frequency-dependent damping or a calibration curve, based on the reference measurements, in order to form a comparison and determine whether the pipette contains fluid or has made contact with the fluid,
   wherein said additional mass is configured to increase the amount of change in the frequency-dependent damping of the ultrasonic signal in the wall of the suction tube when the pipette contains fluid or has made contact with the fluid.

2. The method according to claim 1, wherein the same pipette that was used for the at least one reference measurement is used for the method as set forth in claim 1.

3. The method according to claim 1, wherein the frequency-dependent damping is measured continuously.

4. The method according to claim 1, wherein the frequency-dependent damping is evaluated in a predefined frequency range, in which there is at least one eigen mode of the measured ultrasonic signal.

5. The method according to claim 4, wherein for the comparison the resonant frequency of at least one eigen mode is compared.

6. The method according to claim 4, wherein for the comparison the resonance amplitude of at least one eigen mode is compared.

7. The method according to claim 1, wherein the ultrasonic signal is coupled into the wall of the suction tube in such a way that the transversal modes are excited.

8. The method according to claim 1, wherein the piezo actuator is also used for receiving the damped ultrasonic signal.

9. The method according to claim 1 wherein the ultrasonic frequencies, which are used for measuring the frequency-dependent damping, are selected from a range of 1 to 10 times the quotient composed of the speed of sound in the pipette material and a characteristic geometric expansion of the pipette.

10. The method according to claim 9, wherein the characteristic geometric expansion of the pipette is the length of the pipette.

11. The method according to claim 1, wherein the pipette is an at least two-part pipette wherein a first part comprises the suction tube and a second part comprises the pipette tip.

12. The method according to claim 11, wherein the pipette tip is a disposable element.

13. The method according to claim 11, wherein the frequency-dependent damping signal is used to determine whether the pipette is complete and whether the second part of the pipette is present.

14. The method according to claim 11, wherein the second part of the at least two-part pipette is detachable from the first part.

15. The method according to claim 1, wherein the piezo actuator comprises a ceramic made of lead, zirconate and titanate (PZT).

16. The method according to claim 1, wherein the piezo actuator is mounted on the outside of the wall of the suction tube.

17. The method according to claim 1, wherein the additional mass is in a range between 0.1 and 10 times the weight of the suction tube.

18. The method according to claim 1, wherein the additional mass is adhesively cemented on the side of the piezo actuator that faces away from the suction tube.

19. A pipetting method for pipetting fluid with a pipette, the pipette comprising a suction tube and a pipette tip, the method comprising:
   immersing the pipette tip into the fluid, and
   aspirating the fluid into the pipette tip,
   wherein the method according to claim 1 is used to check whether the pipette tip is making contact with the fluid, and following the step of immersing the pipette tip, whether the fluid is aspirated into the pipette tip.

20. The pipetting method according to claim 19, wherein the pipette tip is lowered in the direction of the fluid from a point above the surface of the fluid to be pipetted, and during this lowering operation the frequency-dependent damping is measured in a predefined frequency range comprising a plurality of frequencies, in order to determine the point in time, at which the pipette tip strikes the fluid surface, from a change in the frequency-dependent damping signal.

21. The pipetting method according to claim 19, wherein the immersion depth of the pipette in the fluid is concluded from the frequency-dependent damping signal.

22. The method according to claim 21, wherein the immersion depth of the pipette in the fluid is concluded from the frequency-dependent damping signal through comparison with at least one reference measurement.

23. The method according to claim 21, wherein the immersion depth of the pipette in the fluid is concluded from the frequency-dependent damping signal through a comparison with reference measurements, which are combined to construct a calibration curve.

24. The pipetting method according to claim 19 wherein the functionality of the pipette is tested with the method according to claim 1.

25. A pipetting method for pipetting fluid with a pipette, the pipette comprising a suction tube and a pipette tip, the method comprising:
immersing the pipette tip into the fluid, and
aspirating the fluid into the pipette;
wherein the method according to claim 1 is used to determine whether the pipette tip contains fluid, and wherein the amount of fluid in the pipette is concluded from the frequency-dependent damping signal.

26. The method according to claim 25, wherein the amount of fluid in the pipette is concluded from the frequency-dependent damping signal through comparison with at least one reference measurement.

27. The method according to claim 25, wherein the amount of fluid in the pipette is concluded from the frequency-dependent damping signal through comparison with reference measurements which are combined to construct a calibration curve.

28. A pipetting method for pipetting fluid with a pipette, the pipette comprising a suction tube and a pipette tip, the method comprising:
immersing the pipette tip into the fluid, and
aspirating a fluid into the pipette;
wherein the method according to claim 1 is used to determine whether the pipette contains fluid, and wherein the type of fluid in the pipette is concluded from the frequency-dependent damping signal.

29. The method according to claim 28, wherein the type of fluid in the pipette is concluded from the frequency-dependent damping signal through comparison with at least one reference measurement.

30. A pipetting method for pipetting fluid with a pipette, the pipette comprising a suction tube and a pipette tip, the method comprising:
immersing the pipette tip into the fluid;
aspirating the fluid into the pipette; and
dispensing the fluid from the pipette;
wherein the method according to claim 1 is used to verify whether the pipette is totally emptied after the pipetting operation.

31. A suction tube arrangement for a pipetting device for pipetting fluid, comprising:

an ultrasonic transducer disposed between a suction tube and an additional mass, said ultrasonic transducer mounted on said suction tube to couple an ultrasonic signal into the wall of said suction tube, wherein said ultrasonic transducer is in contact with said additional mass, said additional mass provided on the side of the ultrasonic transducer that faces away from the suction tube;
an actuating device for actuating the ultrasonic transducer in order to output an ultrasonic signal in a predefined frequency range comprising a plurality of frequencies;
a receiving device for receiving a damped ultrasonic signal in the wall of the suction tube as a function of frequency in the predefined frequency range; and
a suction device for generating a negative pressure in the suction tube, in order to aspirate fluid into or through the suction tube,
wherein said additional mass is configured to increase the amount of change in the frequency-dependent damping of the ultrasonic signal in the wall of the suction tube when the pipetting device contains fluid or has made contact with fluid.

32. The suction tube arrangement according to claim 31, wherein the suction device comprises a pipette suction piston, which is guided in the suction tube.

33. The suction tube arrangement according to claim 31, wherein the ultrasonic transducer and the actuating device are configured in such a way that they can output a wideband ultrasonic signal, and the receiving device is configured in such a way that it can receive a wideband ultrasonic signal.

34. The suction tube arrangement according to claim 33, further comprising an evaluating unit for evaluating the damped ultrasonic signal as a function of the frequency.

35. The suction tube arrangement according to claim 34, wherein evaluating the damped ultrasonic signal as a function of the frequency is with respect to the resonant frequency, the resonant amplitude, or both the resonant frequency and the resonant amplitude of the wideband ultrasonic signal.

36. The suction tube arrangement according to claim 31, wherein the ultrasonic transducer and the actuating device are configured for outputting a variable ultrasonic signal, and the receiving device is configured for receiving a variable ultrasonic signal.

37. The suction tube arrangement according to claim 31, further comprising a memory unit for storage of data from reference measurements of the damped ultrasonic signal.

38. The suction tube arrangement according to claim 31, wherein the additional mass is in the range between 0.1 and 10 times the weight of the suction tube.

39. The suction tube arrangement according to claim 38, wherein the additional mass is in the range between 0.5 and 2 times the weight of the suction tube.

40. The suction tube arrangement according to claim 31, wherein the ultrasonic transducer is a piezo actuator.

41. A pipetting device comprising a suction tube arrangement according to claim 31.

42. The pipetting device according to claim 41, further comprising an at least two-part pipette, where a first part comprises the suction tube arrangement according to claim 31, and a second part comprises a pipette tip.

43. The pipetting device according to claim 42, wherein the at least two parts are detachable from each other.

44. The suction tube arrangement according to claim 31, wherein the additional mass is adhesively cemented on the ultrasonic transducer.

* * * * *